US011786566B2

(12) United States Patent
Jin et al.

(10) Patent No.: US 11,786,566 B2
(45) Date of Patent: Oct. 17, 2023

(54) ***BIFIDOBACTERIUM ANIMALIS* AND APPLICATION OF COMPOUND BACTERIUM PREPARATION PREPARED FROM *BIFIDOBACTERIUM ANIMALIS* IN PREPARING MEDICINE FOR TREATING OR PREVENTING AVIAN INFLUENZA VIRUS INFECTION**

(71) Applicant: Huazhong Agricultural University, Hubei (CN)

(72) Inventors: Meilin Jin, Hubei (CN); Qiang Zhang, Hubei (CN); Xiaotong Hu, Hubei (CN); Li Yang, Hubei (CN); Jin Hu, Hubei (CN); Ting Wang, Hubei (CN); Xiaomei Sun, Hubei (CN); Zhong Zou, Hubei (CN); Wenxiao Gong, Hubei (CN); Xian Lin, Hubei (CN)

(73) Assignee: Huazhong Agricultural University, Hubei (CN)

(*) Notice: Subject to any disclaimer, the term of this patent is extended or adjusted under 35 U.S.C. 154(b) by 140 days.

(21) Appl. No.: 17/141,104

(22) Filed: Jan. 4, 2021

(65) Prior Publication Data
US 2021/0213075 A1 Jul. 15, 2021

(30) Foreign Application Priority Data
Jan. 13, 2020 (CN) .......................... 202010031196.6

(51) Int. Cl.
*A61K 35/745* (2015.01)
*A61P 31/16* (2006.01)

(52) U.S. Cl.
CPC ............ *A61K 35/745* (2013.01); *A61P 31/16* (2018.01)

(58) Field of Classification Search
None
See application file for complete search history.

(56) References Cited

PUBLICATIONS

Guo, Huihui et al., "Effect of Bifidobacterium on intestinal injury caused by ulcerative colitis and intestinal flora in mice," Shiyanyanjiu (Experimental Research), 2017-13, pp. 60-62 (2017).
Alvin Ibarra et al., "Effects of 28-day *Bifidobacterium animalis* subsp.lactis HN019 supplementation on colonic transit time and gastrointestinal symptoms in adults with functional constipation: A double-blind, randomized, placebo-controlled, and dose-ranging trial," Gut Microbes, 9:3, pp. 236-251, DOI: 10.1080/19490976. 2017.1412908 (2018).
Gloria Solano-Aguilar et al, "*Bifidobacterium animalis* subspecies lactis modulates the local immune response and glucose uptake in the small intestine of juvenile pigs infected with the parasitic nematode Ascaris suum," Gut Microbes, 9:5, 422-436, DOI: 10.1080/19490976.2018.1460014 (2018).
Hüseyin Sancar Bozkurt et al., "*Bifidobacterium animalis* subspecies lactis engineered to produce mycosporin-like amino acids in colorectal cancer prevention," Sage Open Medicine, vol. 7, pp. 1-5 (2019).
Jung Min Chae et al., "Effects of Orally-Administered *Bifidobacterium animalis* subsp. lactis Strain BB12 on Dextran Sodium Sulfate-Induced Colitis in Mice," J. Microbiol. Biotechnol., 28(11), pp. 1800-1805 (Sep. 20, 2018).

*Primary Examiner* — Jana A Hines
*Assistant Examiner* — Khatol S Shahnan Shah
(74) *Attorney, Agent, or Firm* — MEI & MARK LLP; Manni Li (57) ABSTRACT

*Bifidobacterium animalis* and application of a compound bacterium preparation prepared from the *Bifidobacterium animalis* in the preparation of a medicine for treating or preventing avian influenza virus infection. The invention discovers that *Bifidobacterium animalis* ATCC Accession No. 25527 can be used for treating animals infected by H7N9, and after the *Bifidobacterium animalis* ATCC Accession No. 25527 is compounded with *Bifidobacterium pseudolongum* ATCC Accession No. 25526, the effect is better. The compound preparation can regulate the body immune response, remarkably improve the weight loss and lung tissue injury caused by H7N9 influenza virus infection, and obviously improve the survival rate of mice infected by H7N9 influenza virus. The compound probiotic preparation provided by the invention has a remarkable effect of resisting H7N9 influenza virus infection, and can be effectively used for preventing and treating avian influenza virus infection.

4 Claims, 11 Drawing Sheets

BIFIDOBACTERIUM ANIMALIS AND APPLICATION OF COMPOUND BACTERIUM PREPARATION PREPARED FROM BIFIDOBACTERIUM ANIMALIS IN PREPARING MEDICINE FOR TREATING OR PREVENTING AVIAN INFLUENZA VIRUS INFECTION

CROSS-REFERENCE TO RELATED APPLICATIONS

The subject application claims priority on Chinese Application No. CN202010031196.6 filed on Jan. 13, 2020 in China. The contents and subject matter of the Chinese priority application is incorporated herein by reference.

BACKGROUND OF THE INVENTION

Technical Field

The invention relates to the field of biological preparations against influenza virus infections, in particular to *Bifidobacterium animalis* and an application of a compound bacterium preparation prepared from the *Bifidobacterium animalis* in preparation of a medicine for treating or preventing avian influenza virus infection.

Description of Related Art

Avian influenza virus belongs to the Orthomyxoviridae Influenza A virus genus and is a highly contagious infectious disease worldwide. The disease mainly occurs in poultry and wild birds, seriously hindering the development of the poultry industry. Moreover, some of its subtypes (H5, H7, H9, H10) can also transmit to people cross-species, causing fever, cough, muscle aches, conjunctivitis, respiratory diseases and other symptoms, and even death in severe cases, posing a serious threat to human health.

The avian influenza virus has always been relatively mild and only spreads among animals. However, human cases of H7N9 influenza were first detected in Shanghai and Anhui in March 2013, proving that this virus is able to spread from poultry to humans across species isolation. Poultry hosts infected with H7N9 include chickens, ducks, geese, and quails, and wild hosts include waterfowls around rivers, lakes, and seas, as well as various migratory wild birds. Close contact with infected poultry, its secretions and excrement, or the virus-contaminated environment can cause human infection with H7N9 avian influenza virus. According to statistics from the World Health Organization (WHO), as of March 2018, the number of people infected with H7N9 worldwide has reached 1,564. Among them, a total of 1,438 cases and 570 deaths have been reported in China, with a fatality rate high up to 39.63%. Therefore, well prevention and control of avian influenza H7N9 can not only promote the healthy development of the livestock and poultry breeding industry, but also effectively maintain social and economic stability and ensure public health safety.

At present, the prevention and control technologies for avian influenza at home and abroad mainly include: culling, disinfection, biological safety, and vaccination. Although culling infected livestock and poultry can curb the spread of avian influenza to a certain extent, wild birds, as another important host of avian influenza, are difficult to control through culling. Moreover, large-scale culling of livestock and poultry will also cause huge economic losses. Another effective measure to prevent the occurrence of avian influenza is vaccination. When the vaccine strain is the same as the clinically epidemic strain, the ideal protective effect can be obtained, but when the vaccine strain is different from the epidemic strain, it cannot provide effective immune protection. There are many serotypes of the avian influenza virus, and the mixed infection of influenza A viruses of different subtypes often occurs genetic recombination to form new avian influenza viruses, which brings great difficulties to the development and application of vaccines. Immunization failures caused when vaccines used are different from epidemic strains often occur in production practice.

Therefore, in the process of preventing avian influenza, in addition to strengthening vaccine development, other biological preparations with highly effective anti-flu effects should also be actively developed. *Bifidobacterium* are generally considered to be probiotics. When a sufficient amount of Bifidobacteria is ingested, Bifidobacteria can promote the health of the body. It was reported in references that the intake of *Bifidobacterium* could improve the gastrointestinal environment, prevent and treat some diseases caused by intestinal microecological disorders, including gastrointestinal infections, constipation, irritable bowel syndrome (IBS), inflammatory bowel disease (IBD)), ulcerative colitis, allergies, antibiotic-induced diarrhea, cardiovascular disease, and colorectal cancer. It was reported by Alvin Ibarra et al. (2018) that in a randomized double-blind and placebo-controlled trial, through the evaluation of various related indicators, supplementation of *Bifidobacterium animalis* could improve stool frequency. It was found by Guo Huihui et al. (2017) that *Bifidobacterium* could effectively inhibit the decrease in blood hemoglobin concentration in mice caused by ulcerative colitis and the shortening of colon length caused by ulcerative colitis, and that *Bifidobacterium* took a therapeutic effect on ulcerative colitis by adjusting the intestinal microecological balance. Gloria Solano-Aguilar et al. (2018) reported that feeding subsp. *Lactis* of *Bifidobacterium animalis* had a local immunomodulatory effect on piglets infected with *Ascaris suum*. During nematode infection, by reducing the components of type 2 allergic reactions in pigs, it changed the local immune response and improved intestinal function. Jung Min Chae et al., (2018) reported that subsp. *lactis* BB12 of *Bifidobacterium animalis* could significantly improve DSS-induced colitis, and suggested that probiotic BB12 could improve the survival rate of intestinal cells by regulating the expression of pro-apoptotic cytokines. Hüseyin Sancar Bozkurt et al., (2019) reported that Bifidobacteria could be used for the prevention of colorectal cancer.

Although there are some reports on the prevention and treatment of intestinal infections by *Bifidobacterium*, there are few reports on *Bifidobacterium* as probiotic preparations against intestinal infections, especially against respiratory tract infections. At present, there is no report about the antiviral effect of *Bifidobacterium animalis*. The invention reports the application of *Bifidobacterium animalis* against influenza virus for the first time.

BRIEF SUMMARY OF THE INVENTION

The invention is directed to the difficulty about prevention and treatment of influenza virus infection, and intended to provide the application of *Bifidobacterium animalis* having American Type Culture Collection (ATCC) Accession No. 25527 in the preparation of a medicine for treating or preventing avian influenza virus infection.

Another objective of the invention is to provide a medicine for treating or preventing avian influenza virus infection. The medicine includes *Bifidobacterium animalis* having ATCC Accession No. 25527 and *Bifidobacterium pseudolongum* having ATCC Accession No. 25526.

The final objective of the invention is to provide the application of a preparation comprising *Bifidobacterium animalis* having ATCC Accession No. 25527 and *Bifidobacterium pseudolongum* having ATCC Accession No. 25526 in the preparation of a medicine for treating or preventing avian influenza virus infection.

In order to achieve the above objectives, the invention adopts the following technical measures:

The application of *Bifidobacterium animalis* ATCC Accession No. 25527 in the preparation of a medicine for treating or preventing avian influenza virus infection, including the use of ATCC Accession No. 25527 as the sole active ingredient or one of active ingredients for the preparation of a medicine for treating or preventing diseases with avian influenza virus infection.

In the above-mentioned application, preferably, the effective bacterial concentration of the *Bifidobacterium animalis* is $\geq 1 \times 10^9$ CFU/ml.

A medicine for treating or preventing avian influenza virus infection, including *Bifidobacterium animalis* ATCC Accession No. 25527 and *Bifidobacterium pseudolongum* ATCC Accession No. 25526;

In the above-mentioned medicine, preferably, the ratio of the effective bacterial concentration of the *Bifidobacterium animalis* ATCC Accession No. 25527 to the *Bifidobacterium pseudolongum* ATCC Accession No. 25526 is 1:0.5-2.

In the above-mentioned medicine, the optimal ratio of effective bacterial concentration of *Bifidobacterium animalis* ATCC Accession No. 25527 to *Bifidobacterium pseudolongum* ATCC Accession No. 25526 is 1:1, and the effective bacterial concentration after the mixture of *Bifidobacterium animalis* ATCC Accession No. 25527 and *Bifidobacterium pseudolongum* ATCC Accession No. 25526 is $\geq 1 \times 10^9$ CFU/ml.

The application of the preparation including ATCC Accession No. 25527 and ATCC Accession No. 25526 in the preparation of a medicine for treating and preventing avian influenza virus infection also belongs to the protection scope of the invention;

The preparation including ATCC Accession No. 25527 and ATCC Accession No. 25526 can also be used to prepare interferon stimulants after avian influenza virus infection.

The symptoms of the infection described above include weight loss, death, pathological injury to the lungs, and the proliferation of the avian influenza virus in the lungs due to the avian influenza virus infection.

Oral administration of *Bifidobacterium animalis* ATCC Accession No. 25527 to treat or prevent avian influenza virus infection and oral administration of *Bifidobacterium animalis* ATCC Accession No. 25527 and *Bifidobacterium pseudolongum* ATCC Accession No. 25526 to treat or prevent avian influenza virus infection also fall within the protection scope of the invention.

Oral administration of *Bifidobacterium animalis* ATCC Accession No. 25527 to treat weight loss, death, and lung pathological injury caused by avian influenza virus infection, or the proliferation of H7N9 influenza virus in the lungs;

Oral administration of *Bifidobacterium animalis* ATCC Accession No. 25527 and *Bifidobacterium pseudolongum* ATCC Accession No. 25526 to treat weight loss, death, and lung pathological injury caused by H7N9 infection, or proliferation of avian influenza virus in the lungs.

The avian influenza virus described above is preferably H7N9.

Compared with the prior art, the invention has the following advantages:

(1) The compound probiotic preparation of the invention can regulate the immune response of the host body, promote the expression of multiple cytokines in the early stage of avian influenza virus infection, and increase the body's elimination of the virus; reduce the expression of certain cytokines in the middle of infection and reduce the inflammatory injury caused by overexpression of cytokines.

(2) The probiotic preparation of the invention can quickly improve the ability of the body to produce interferon and clear the virus in time after the animal body is infected with avian influenza virus.

(3) The compound probiotic preparation of the invention can significantly inhibit the proliferation of H7N9 influenza virus in mice, improve the weight loss caused by H7N9 infection, and improve the survival rate of infected mice. Therefore, the compound probiotic preparation has obvious resistance to H7N9 influenza virus infection.

BRIEF DESCRIPTION OF THE SEVERAL VIEWS OF THE DRAWINGS

FIGS. 1A and 1B show the colony morphology of the *Bifidobacterium* used in the present invention, where

FIGS. 6A to 6L show the effect of intragastric administration of the probiotic preparation of the present invention on pathological changes in the lungs of SPF mice infected with H7N9, where FIG. 6A show the effect in Day 0 with PBS; FIG. 6E show the effect in Day 3 with PBS; FIG. 6I show the effect in Day 5 with PBS.

FIGS. 7A to 7F show the effect of intragastric administration of the probiotic preparation of the present invention on the changes of lung cytokines in SPF mice infected with H7N9, where

FIGS. 8A to 8F show the effect of intragastric administration of the probiotic preparation of the present invention on the changes of serum cytokines in SPF mice infected with H7N9, where

DETAILED DESCRIPTION OF THE INVENTION

The experimental methods and conditions in the following examples are conventional methods unless otherwise specified. These examples are only used to illustrate the invention, and the protection scope of the invention is not limited by these examples. The technical solutions of the invention, unless otherwise specified, are conventional solutions in the field; unless otherwise specified, the reagents or materials are all sourced from commercial channels.

The invention takes avian influenza virus H7N9 as an example to illustrate the application of *Bifidobacterium animalis* ATCC Accession No. 25527 and its compound preparation in the preparation of a medicine for preventing or treating avian influenza virus infection.

The following specific embodiments further illustrate the invention:

Example 1

Preparation Method of a Probiotic Preparation Against H7N9 Avian Influenza Virus Infection:

1. Preparation of Single-Bacterium Preparations of *Bifidobacterium animalis* and *Bifidobacterium pseudolongum*

Figure 1A:
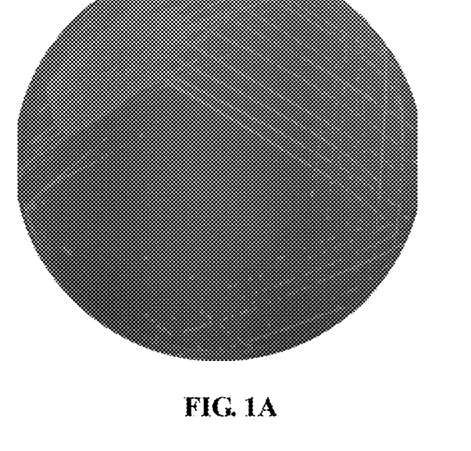
FIG. 1A shows the colony morphology of *Bifidobacterium pseudolongum*.
Figure 1B:
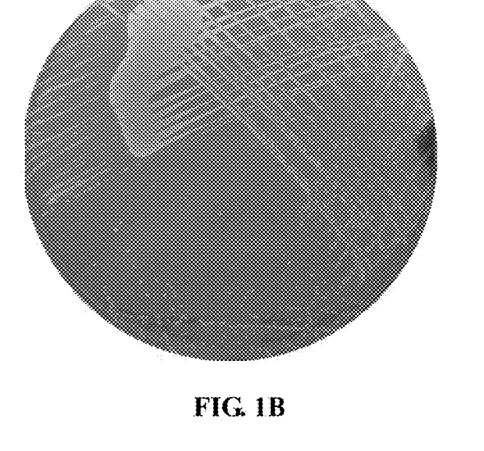
FIG. 1B shows the colony morphology of *Bifidobacterium animalis*.
Figure 2:
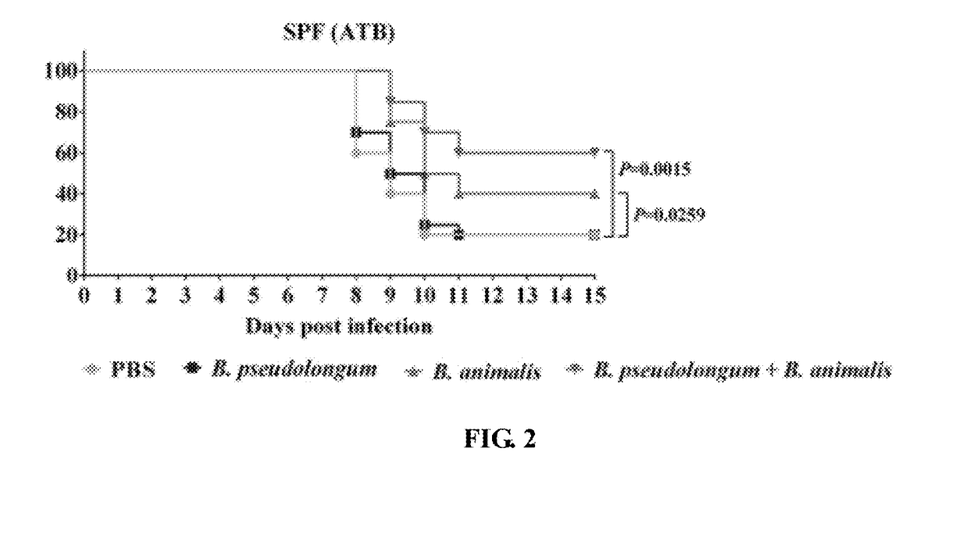
FIG. 2 shows the effect of intragastric administration of the probiotic preparation of the present invention on the survival rate of SPF mice infected with H7N9, where the vertical axis shows the percentage of survival.
Figure 3:
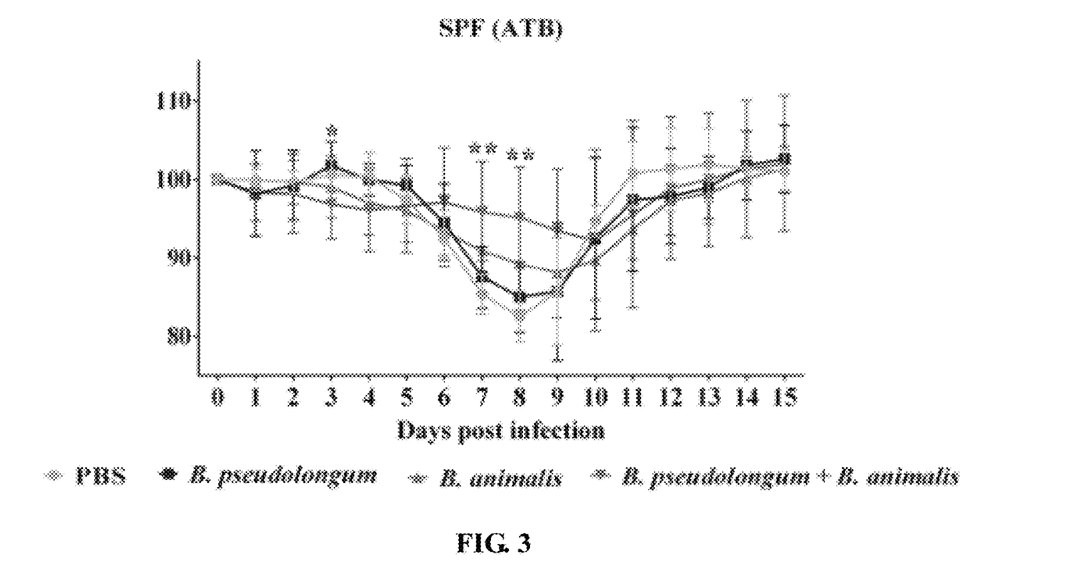
FIG. 3 shows the effect of intragastric administration of the probiotic preparation of the present invention on the weight of SPF mice infected with H7N9, where the vertical axis shows the percentage of the initial weight.

*Bifidobacterium animalis* ATCC Accession No. 25527 and *Bifidobacterium pseudolongum* ATCC Accession No. 25526. The lyophilized powder of the strain was resuspended with germ-free PBS, an appropriate count of bacteria was picked up with an inoculating loop to streak and rejuvenate on an MRS solid plate medium, and cultivated under an anaerobic condition at 37° C. for 24-48 hours. The rejuvenated *Bifidobacterium animalis* and *Bifidobacterium pseudolongum* were respectively cultured in MRS streaks (FIG. 1A, FIG. 1B). After culturing for 24 hours under an anaerobic condition at 37° C., bacterial lawns on the MRS medium plate were washed with PBS to collect the bacterial suspension. The bacterial suspension was centrifuged at 4° C., 5000 rpm for 10 minutes, the supernatant was discarded, the collected *Bifidobacterium animalis* and *Bifidobacterium pseudolongum* precipitate were resuspended in PBS, and viable bacteria were counted on the MRS plate. The concentration of the bacterial suspension was adjusted so that the number of viable bacteria is $1\times10^9$ CFU/ml, and the resulting products were stored as single-bacterium preparations against influenza virus at 4° C. for later use.

2. Preparation Method of Compound Probiotic Preparation Against H7N9 Avian Influenza Virus Infection The single-bacterium preparations prepared by the above method were mixed at a ratio of 1:1 (V/V) to prepare a compound probiotic preparation. The concentrations of *Bifidobacterium animalis* ATCC Accession No. 25527 and *Bifidobacterium pseudolongum* ATCC Accession No. 25526 in the compound probiotic preparation were both $5\times10^8$ CFU/ml, and the total bacterial cell concentration was $1\times10^9$ CFU/ml.

The single and compound bacterium probiotic preparations in Example 1 were used in the following examples.

Example 2

The effect of the probiotic preparation prepared in Example 1 on the mortality and weight of mice after H7N9 avian influenza virus infection 1. Effect on the Mortality and Weight of SPF Mice The test animals were 8-week-old female C57BL/6 SPF (Specific-Pathogen-Free) mice, in a total of 80, randomly divided into 4 groups, 20 in each group, and all the animals were raised in an ABSL3 (Animal Biological Safety Level-3) laboratory. The first group was a germ-free PBS control group in which each mice took 100 ul by intragastric administration; the second group was a *Bifidobacterium pseudolongum* ATCC Accession No. 25526 single-bacterium preparation group in which each mice took 100 ul by intragastric administration; the third group is a *Bifidobac-*

*terium animalis* ATCC Accession No. 25527 single-bacterium preparation group in which each mice took 100 ul by intragastric administration; the fourth group is a *Bifidobacterium animalis* ATCC Accession No. 25527-*Bifidobacterium pseudolongum* ATCC Accession No. 25526 compound preparation group in which each mice took 100 ul by intragastric administration.

Antibiotic treatment: Before intragastric administration of the probiotic preparations to test mice, the mice were treated with a compound antibiotic solution. The compound antibiotic preparation, including ampicillin (1 mg/ml), streptomycin (5 mg/ml), vancomycin (0.25 mg/ml), colistin (1 mg/ml), was added for 3 consecutive days to the germ-free water the mice drank, and the addition of the compound antibiotic preparation was stopped one day before the intragastric administration of a probiotic preparation. All antibiotics were purchased with sigma-Aldrich company.

After intragastric administration of PBS or the probiotic preparations to the mice, all mice were infected with one LD50 H7N9 avian influenza virus intranasally. After influenza virus infection, the mice were observed and weighed for 15 consecutive days, and the survival status was recorded.

Figure 4:
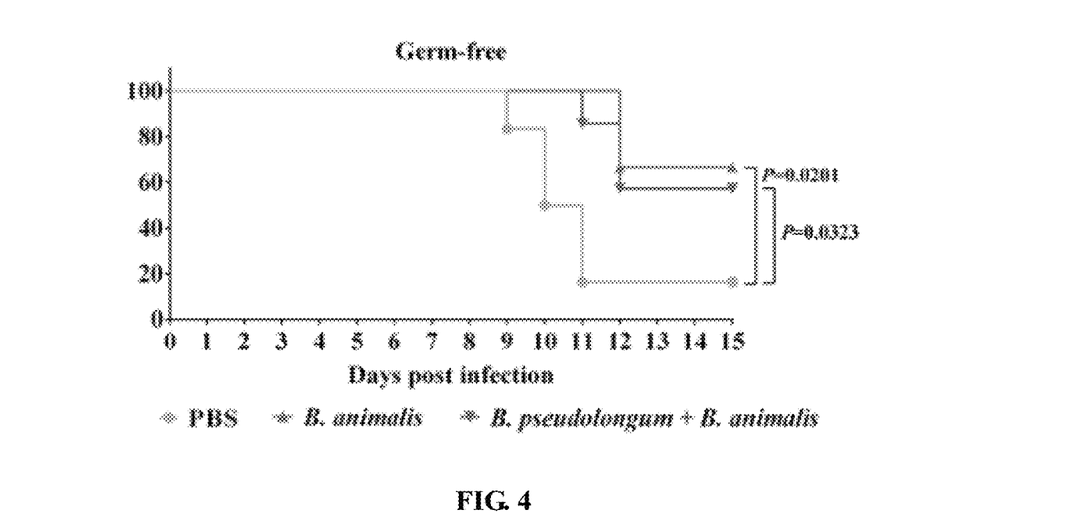
FIG. 4 shows the effect of intragastric administration of the probiotic preparation of the present invention on the survival rate of germ-free mice infected with H7N9, where the vertical axis shows the percentage of survival.
Figure 5:
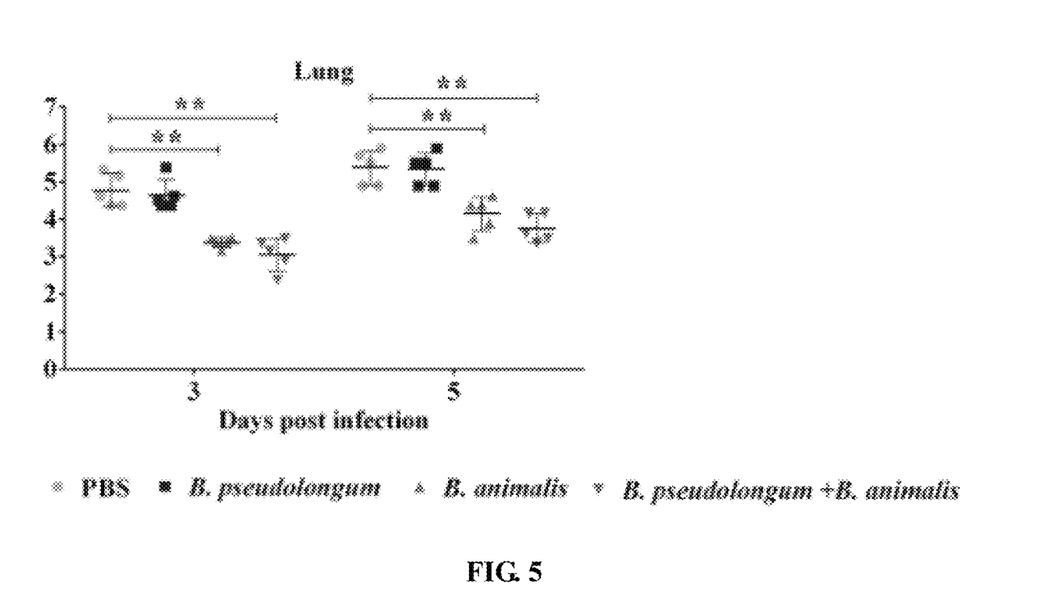
FIG. 5 shows the effect of intragastric administration of the probiotic preparation of the present invention on the proliferation of lung virus in SPF mice infected with H7N9, where the vertical axis shows the virus titer ($Log_{10}$ $EID_{50}$/ml).
Figure 6A:
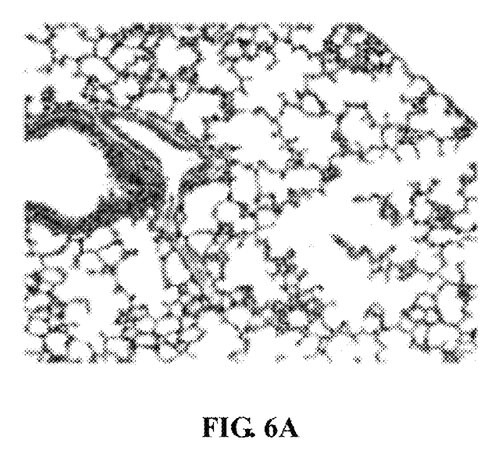
Figure 6B:
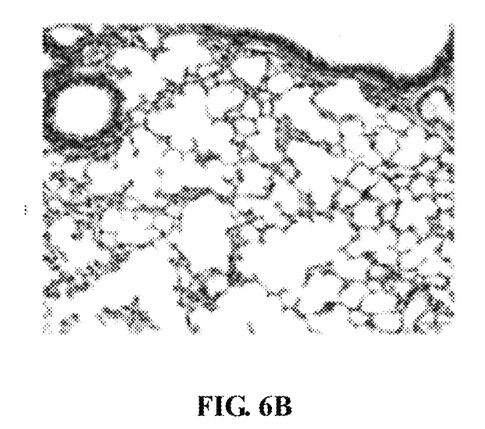
FIG. 6B shows the effect in Day 0 with *Bifidobacterium pseudolongum*.
Figure 6C:
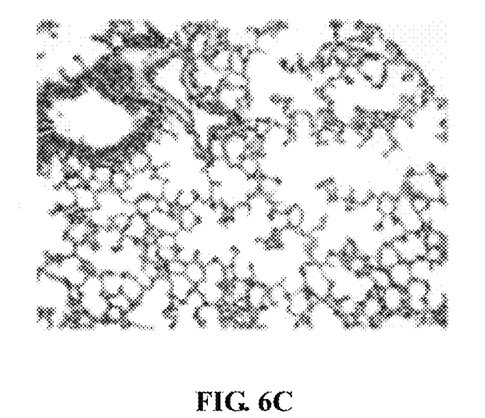
FIG. 6C shows the effect in Day 0 with *Bifidobacterium animalis*.
Figure 6D:
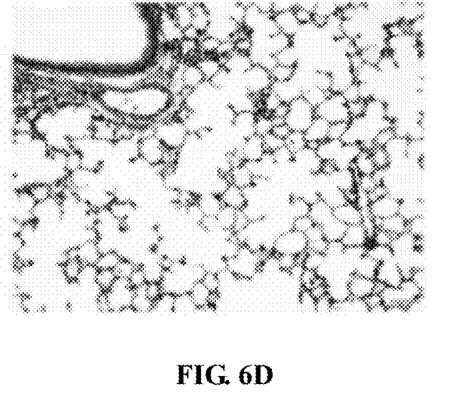
FIG. 6D shows the effect in Day 0 with *Bifidobacterium pseudolongum* and *Bifidobacterium animalis*.
Figure 6E:
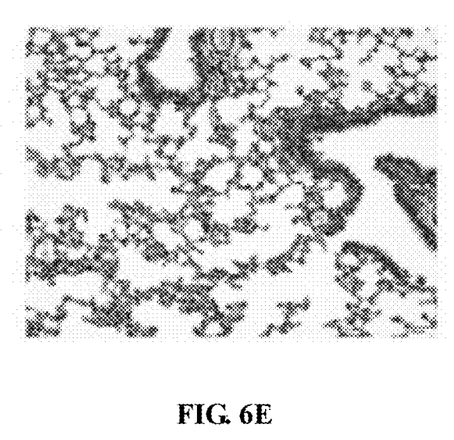
Figure 6F:
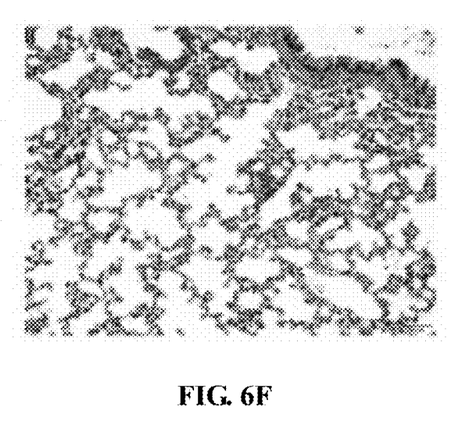
FIG. 6F shows the effect in Day 3 with *Bifidobacterium pseudolongum*.
Figure 6G:
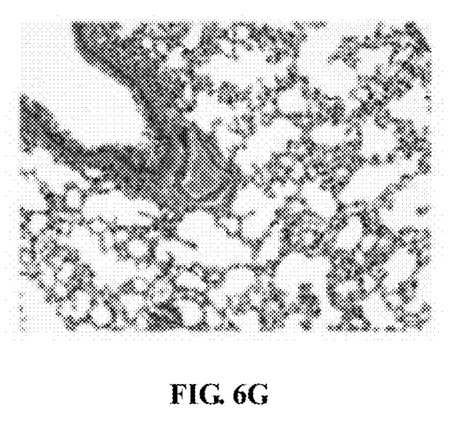
FIG. 6G shows the effect in Day 3 with *Bifidobacterium animalis*.
Figure 6H:
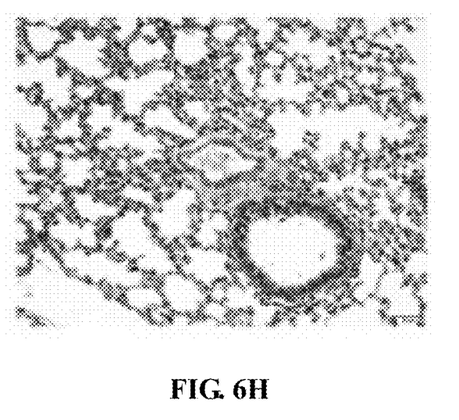
FIG. 6H shows the effect in Day 3 with *Bifidobacterium pseudolongum* and *Bifidobacterium animalis*.
Figure 6I:
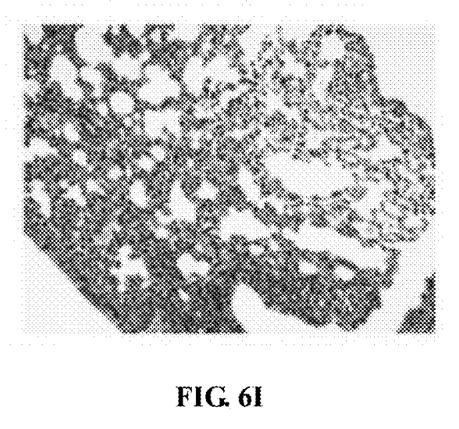
Figure 6J:
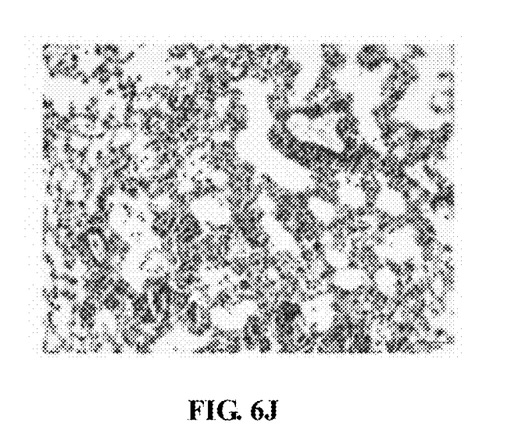
FIG. 6J shows the effect in Day 5 with *Bifidobacterium pseudolongum*.
Figure 6K:
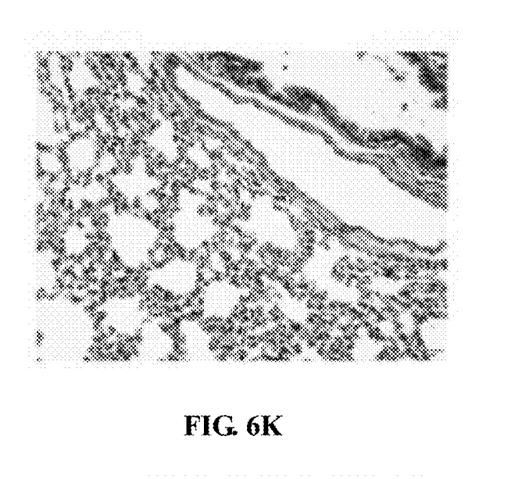
FIG. 6K shows the effect in Day 5 with *Bifidobacterium animalis*.
Figure 6L:
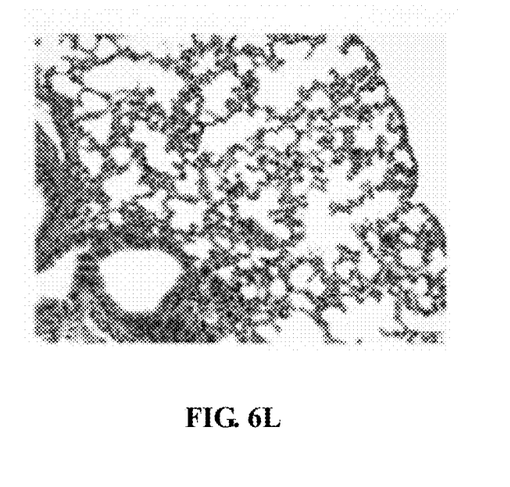
FIG. 6L shows the effect in Day 5 with *Bifidobacterium pseudolongum* and *Bifidobacterium animalis*.
Figure 7A:
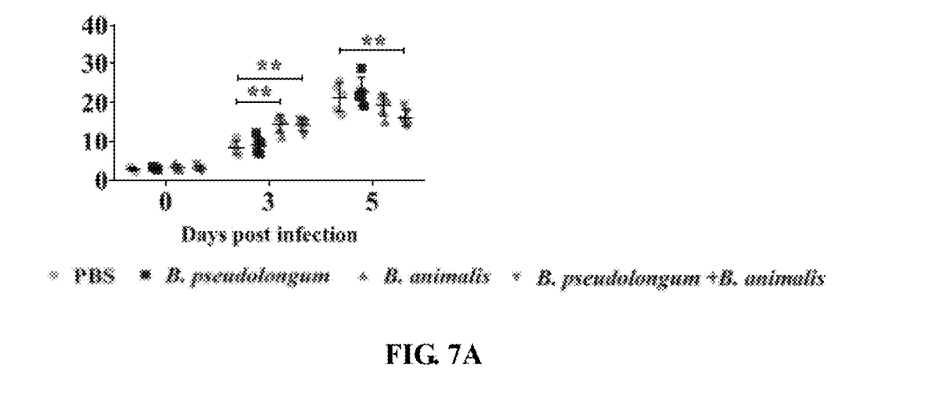
FIG. 7A shows the effect on TNF-α (pg/mL) as represented by the vertical axis.
Figure 7B:
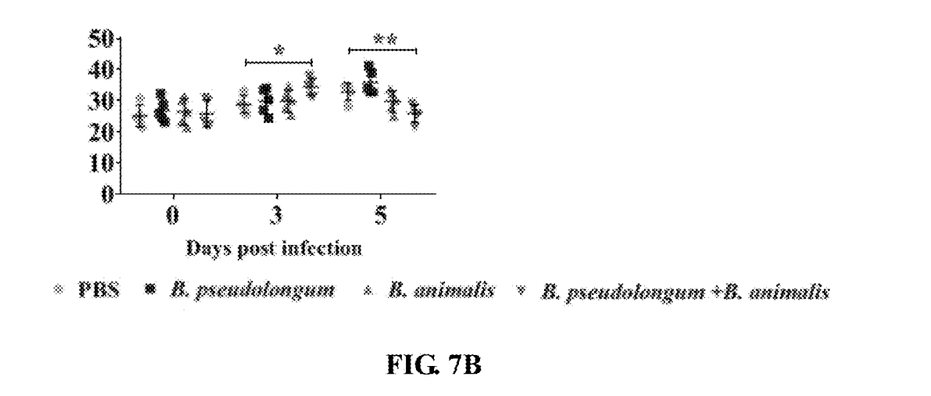
FIG. 7B shows the effect on IL-10 (pg/mL) as represented by the vertical axis.
Figure 7C:
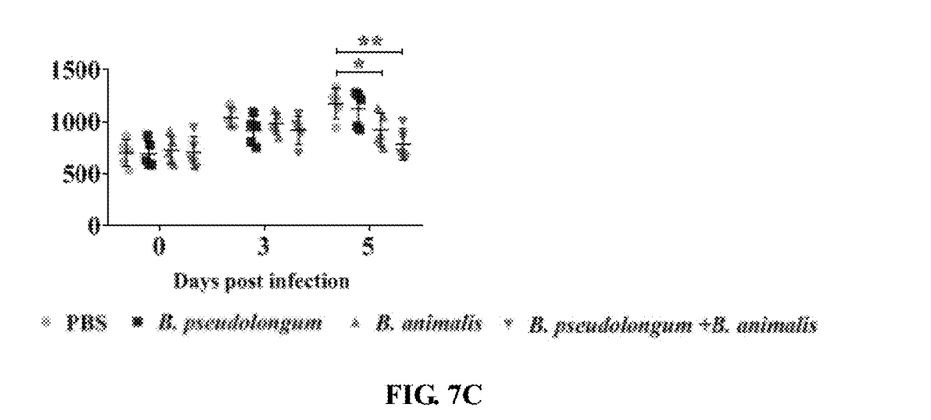
FIG. 7C shows the effect on IL-1β (pg/mL) as represented by the vertical axis.
Figure 7D:
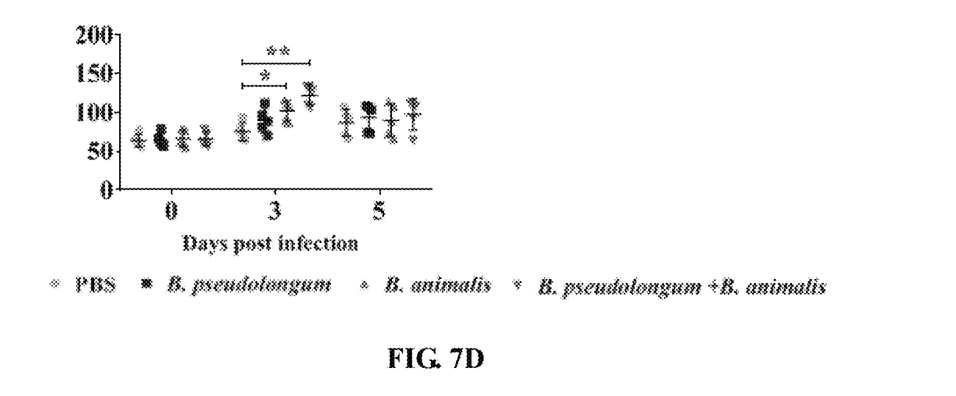
FIG. 7D shows the effect on IFN-γ (pg/mL) as represented by the vertical axis.
Figure 7E:
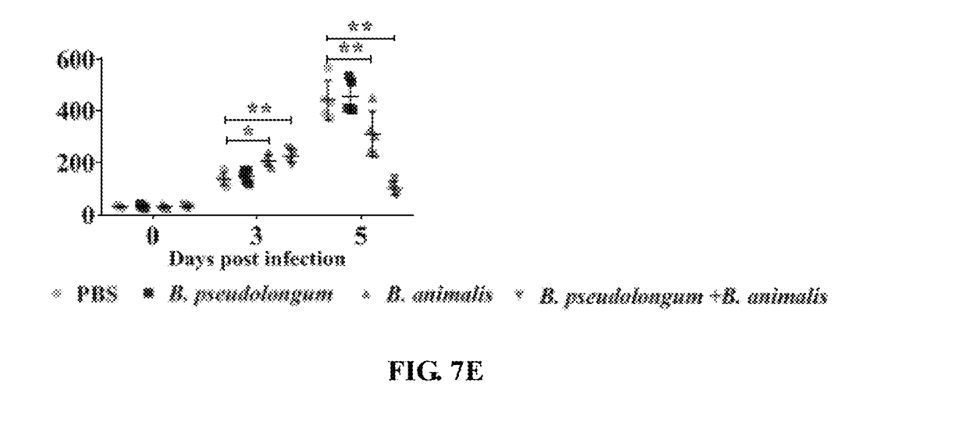
FIG. 7E shows the effect on IL-6 (pg/mL) as represented by the vertical axis.
Figure 7F:
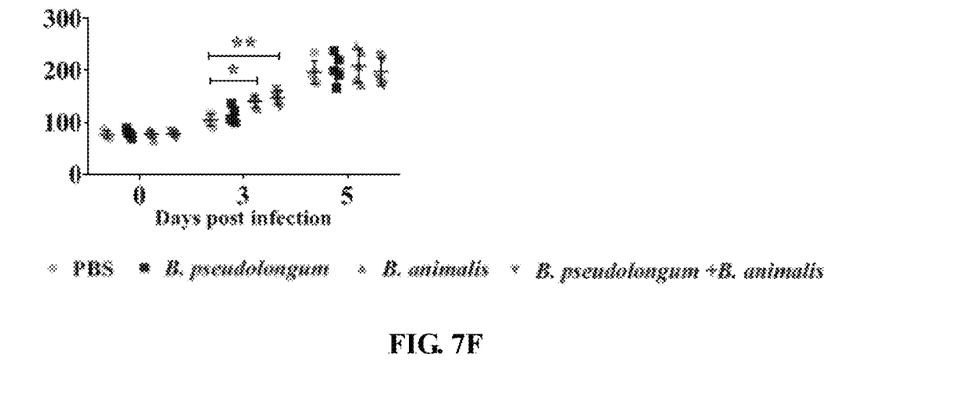
FIG. 7F shows the effect on IFN-β (pg/mL) as represented by the vertical axis.
Figure 8A:
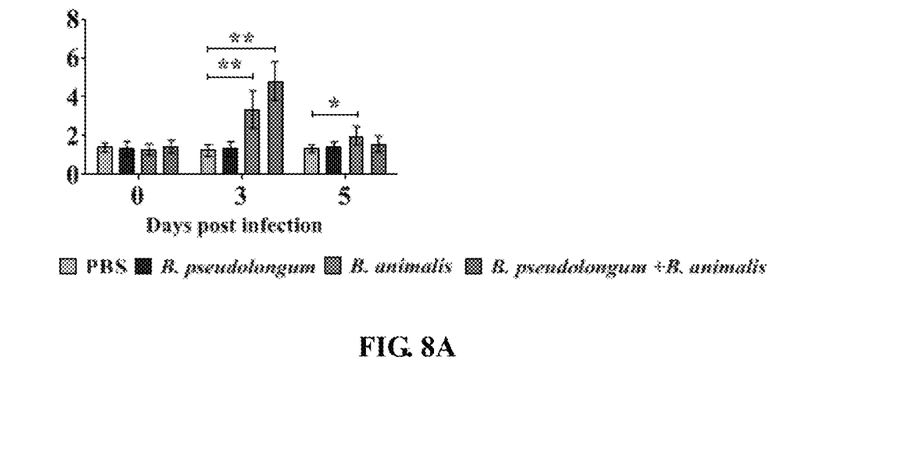
FIG. 8A shows the effect on TNF-α (pg/mL) as represented by the vertical axis.
Figure 8B:
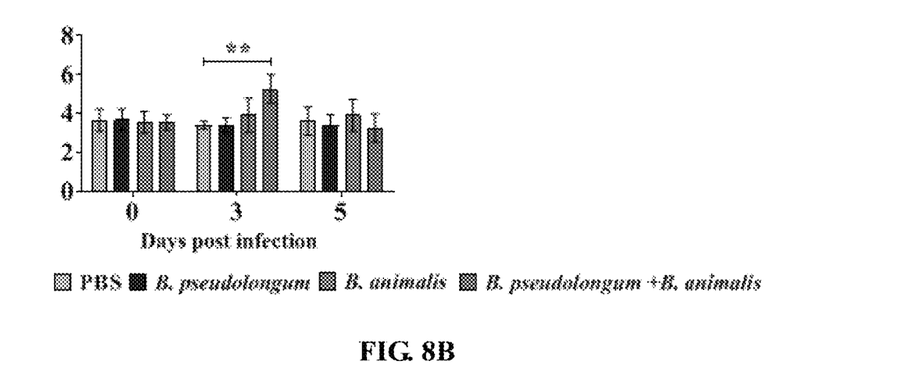
FIG. 8B shows the effect on IL-10 (pg/mL) as represented by the vertical axis.
Figure 8C:
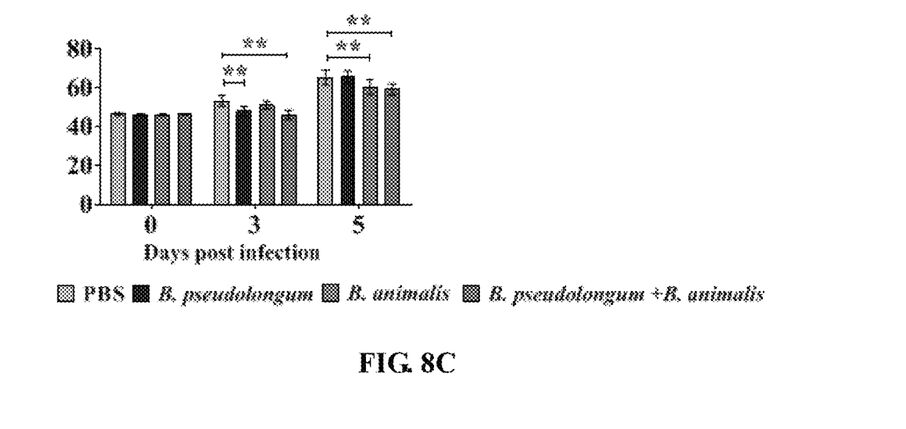
FIG. 8C shows the effect on IL-1β (pg/mL) as represented by the vertical axis.
Figure 8D:
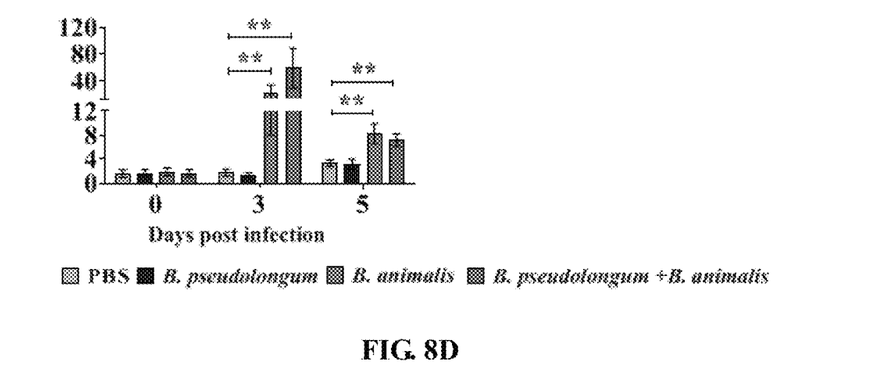
FIG. 8D shows the effect on IFN-γ (pg/mL) as represented by the vertical axis.
Figure 8E:
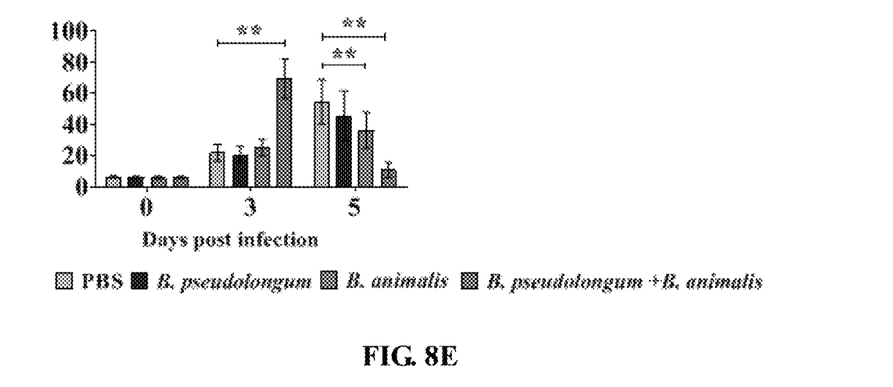
FIG. 8E shows the effect on IL-6 (pg/mL) as represented by the vertical axis.
Figure 8F:
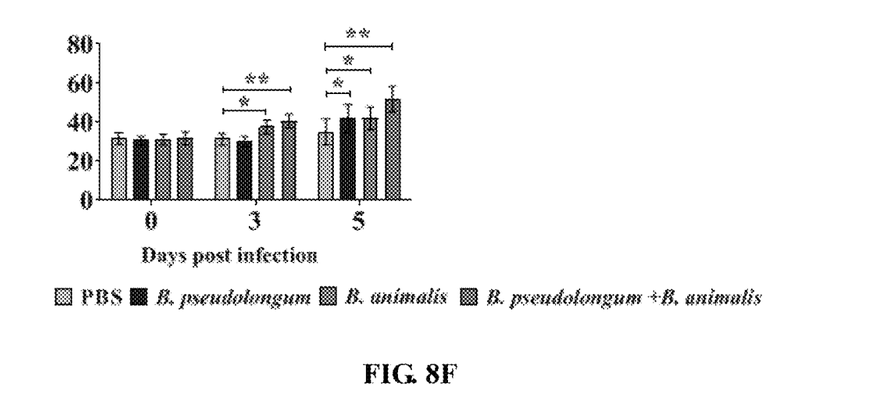
FIG. 8F shows the effect on IFN-β (pg/mL) as represented by the vertical axis.

The results showed that compared with the survival rate of the control group taking intragastric administration of PBS, the survival rate of SPF mice taking intragastric administration of *Bifidobacterium animalis* single-bacterium preparation (P=0.0259) and the survival rate of SPF mice taking the *Bifidobacterium animalis-Bifidobacterium pseudolongum* compound preparation (P=0.0015)) can both be significantly increased by 20% and 40% respectively after the mice were infected with H7N9 avian influenza virus; however, the intragastric administration of the *Bifidobacterium pseudolongum* single-bacterium preparation has no obvious effect on mice infected with H7N9 influenza virus (Table 1, FIG. 2).

TABLE 1

Effect of the probiotic preparations on the survival rate of SPF mice infected with H7N9 influenza virus

| Group | PBS control | *B. pseudolongum* | *B. animalis* | *B. animalis* + *B. pseudolongum* |
|---|---|---|---|---|
| Number at time of infection | 20 | 20 | 20 | 20 |
| Number of survivals 15 days post infection | 4 | 4 | 8 | 12 |
| Survival rate (%) | 20 | 20 | 40 | 60 |
| Mortality | 80 | 80 | 60 | 40 |

In terms of weight, mice taking intragastric administration of the *Bifidobacterium animalis-Bifidobacterium pseudolongum* compound preparation were significantly improved in weight loss 6-10 days after being infected with H7N9 influenza virus. Mice taking the intragastric administration of the *Bifidobacterium pseudolongum* single-bacterium preparation were significantly improved in weight loss to a certain extent 6-10 days after being infected with H7N9 influenza virus (Table 2, FIG. 3).

TABLE 2

Effect of the probiotic preparations on the weight of SPF mice infected with H7N9 influenza virus

| | Weight percentage (%) | | | |
|---|---|---|---|---|
| Number of days | PBS control group | *B. pseudolongum* group | *Bifidobacterium animalis* group | *B. animalis* + *B. pseudolongum* group |
| 0 | 100 | 100 | 100 | 100 |
| 1 | 99.95 ± 1.27 | 98.21 ± 5.40 | 99.98 ± 2.04 | 98.36 ± 3.61 |
| 2 | 99.66 ± 1.34 | 99.23 ± 4.40 | 99.69 ± 2.76 | 98.18 ± 4.98 |
| 3 | 100.64 ± 1.81 | 101.79 ± 3.00 | 99.05 ± 3.88 | 96.91 ± 4.43 |
| 4 | 100.30 ± 2.90 | 99.99 ± 2.01 | 97.08 ± 4.13 | 96.20 ± 5.33 |
| 5 | 97.43 ± 2.88 | 99.26 ± 2.54 | 96.09 ± 4.03 | 96.69 ± 5.94 |
| 6 | 92.58 ± 3.37 | 94.57 ± 4.86 | 93.42 ± 4.59 | 97.14 ± 6.82 |
| 7 | 85.31 ± 2.37 | 87.53 ± 3.97 | 90.96 ± 5.46 | 95.95 ± 6.31 |
| 8 | 82.53 ± 2.88 | 84.99 ± 4.49 | 89.18 ± 5.88 | 95.18 ± 6.38 |
| 9 | 85.71 ± 6.87 | 85.71 ± 8.75 | 88.03 ± 5.64 | 93.45 ± 7.90 |
| 10 | 94.78 ± 1.97 | 92.49 ± 10.29 | 89.71 ± 5.11 | 92.22 ± 11.51 |
| 11 | 100.81 ± 4.04 | 97.43 ± 9.25 | 93.68 ± 3.92 | 95.59 ± 11.95 |
| 12 | 101.38 ± 5.26 | 97.86 ± 6.02 | 97.38 ± 4.48 | 98.89 ± 9.07 |
| 13 | 101.93 ± 4.72 | 98.98 ± 3.94 | 98.25 ± 3.95 | 100.02 ± 8.44 |
| 14 | 101.41 ± 2.08 | 101.83 ± 4.38 | 100.18 ± 2.73 | 101.36 ± 8.73 |
| 15 | 101.09 ± 2.62 | 102.61 ± 4.34 | 101.37 ± 2.78 | 102.06 ± 8.60 |

2. Effect on Mortality of Germ-Free Mice

According to the effects of the aforementioned probiotic preparations on the mortality and weight of SPF mice infected with H7N9 influenza virus, 19 germ-free mice were used in this test to detect the effects of the probiotic preparations in Example 1 on germ-free mice infected with H7N9 avian influenza virus; the 19 germ-free mice were randomly divided into 3 groups. The first group of 6 mice was a germ-free PBS control group in which each mice took 100 ul by intragastric administration; the second group of 6 mice was a *Bifidobacterium animalis* ATCC Accession No. 25527 single-bacterium preparation group in which each mice took 100 ul by intragastric administration; and the third group of 7 mice was a *Bifidobacterium animalis* ATCC Accession No. 25527-*Bifidobacterium pseudolongum* ATCC Accession No. 25526 compound preparation group in which each mice took 100 ul by intragastric administration. Antibiotic treatment was the same as that for SPF mice. One day after intragastric administration of PBS or the probiotic preparations to the mice, all the mice were intraperitoneally injected with 0.5 LD50 dose of H7N9 avian influenza virus. After infection, the status of germ-free mice was observed for 15 consecutive days and the survival status was recorded.

According to the effect of the probiotic preparations of the invention on the survival rate of SPF mice infected with H7N9 influenza virus, the intragastric administration of the *Bifidobacterium animalis* single-bacterium preparation and the compound preparation can significantly improve the survival rate of the mice. In order to further eliminate the influence of microorganisms remaining in the intestinal tract after antibiotic treatment, germ-free mice were used for animal experiments in this example. The results also showed that the survival rates of germ-free mice taking the intragastric administration of the *Bifidobacterium animalis* single-bacterium preparation (P=0.0201) and taking intragastric administration of *Bifidobacterium animalis-Bifidobacterium pseudolongum* compound preparation (P=0.0323) were both improve significantly by 50% and 40.47% respectively as compared with that of the PBS control group. Through comparison of the results of SPF mice and germ-free mice, the only difference is that in the germ-free mice, the protective effect of the intragastric administration of *Bifidobacterium animalis* (66.67%) was even slightly higher than that of the compound preparation (57.14%), but in the SPF mice, the protective effect for the group taking the intragastric administration of *Bifidobacterium animalis* was only half of that for the group taking the intragastric administration of the compound preparation. These results showed that the intragastric administration of *Bifidobacterium animalis* to animals could enhance their resistance to H7N9 influenza virus infection. For non-germ-free animals, additional use of *Bifidobacterium pseudolongum* could enhance this protective effect (Table 3, FIG. 4).

TABLE 3

Effect of the probiotic preparations on the survival rate of germ-free mice infected with H7N9 influenza virus

| Group | PBS control group | *Bifidobacterium animalis* group | *B. animalis* + *B. pseudolongum* group |
|---|---|---|---|
| Number at the time of infection | 6 | 6 | 7 |
| Number of survivals 15 days post infection | 1 | 4 | 4 |
| Survival rate (%) | 16.67 | 66.67 | 57.14 |
| Mortality | 83.33 | 33.33 | 42.86 |

Example 3

The effect of the probiotic preparations prepared in Example 1 on the content of influenza virus in the lungs, the structure of lung tissue, and the content of lung cytokines and blood cytokines in mice infected with H7N9 avian influenza virus 96 SPF mice were randomly divided into 4 groups, 24 mice in each group. The first group was a germ-free PBS control group in which each mice took 100 ul by intragastric administration; the second group was a *Bifidobacterium pseudolongum* ATCC Accession No. 25526 single-bacterium preparation group in which each mice took 100 ul by intragastric administration; the third group is a *Bifidobacterium animalis* ATCC Accession No. 25527 single-bacterium preparation group in which each mice took 100 ul by intragastric administration; the fourth group is a *Bifidobacterium animalis* ATCC Accession No. 25527-*Bifidobacterium pseudolongum* ATCC Accession No. 25526 compound preparation group in which each mice took 100 ul by intragastric administration.

As in Example 2, all SPF mice were raised in an ABSL3 laboratory, and subjected to the same antibiotic treatment, intragastric administration of probiotic preparations and H7N9 influenza virus infection.

After influenza virus infection, blood was collected on day 0, day 3, and day 5, and lung samples were taken by anatomy. There were 8 mice in each group. Five of the eight lung samples of each group were used to determine cytokine content and influenza virus content, and the remaining three lung samples were fixed with 4% formaldehyde solution for tissue section observation.

Blood sample treatment: The collected non-anticoagulated blood samples were rested at 4° C. overnight; after the serum was separated, the serum was centrifuged at 4° C., 1000 rpm for 5 minutes, and the supernatant was taken and frozen at −80° C. for detection of cytokine content.

Lung tissue treatment: the collected lung tissue samples were added with 1 ml germ-free PBS (1 ml PBS/lung) and homogenized and broken by a homogenizer, and centrifuged to take the supernatant; the supernatant was frozen at −80° C. for detection of cytokine content and influenza virus content.

The cytokines tested included TNF-α, IL-1β, IL-6, IL-10, IFN-γ, and IFN-β. Among them, TNF-α, IL-1β, IL-6, IL-10, and IFN-γ were detected by Magnetic Luminex® Assay multiplex kit (R & D Systems), and IFN-β was detected by VeriKine Mouse IFN-β enzyme-linked immunosorbent assay kit (BioLegend).

1. Table 2 Effect of the probiotic preparations on the content of influenza virus in the lungs of mice infected with H7N9 avian influenza virus: The preserved lung tissue homogenate supernatant was inoculated into 9-11 days old SPF chicken embryos for the determination of the influenza virus content in lung tissue. After the inoculated chicken embryos were incubated at 37° C. for 72 hours, and the allantoic fluid was collected for hemagglutination test. The virus titer was calculated using the method described by Reed and Muench.

The test results showed that on day 3 and day 5 post H7N9 influenza virus infection, compared with the PBS control group, the group taking intragastric administration of *Bifidobacterium animalis* single-bacterium preparation and the group taking intragastric administration of *Bifidobacterium animalis-Bifidobacterium pseudolongum* compound preparation were significantly reduced in virus content in the lung tissue; however, the intragastric administration of the *Bifidobacterium pseudolongum* single-bacterium preparation had no effect on the virus content in the lung tissue (Table 4, FIG. 5).

TABLE 4

Effect of probiotic preparations on influenza virus content in lungs of mice infected with H7N9 avian influenza virus ($log_{10}EID_{50}$/ml)

| Group | PBS control | *Bifidobacterium pseudolongum* | *Bifidobacterium animalis* | *B. animalis + B. pseudolongum* |
|---|---|---|---|---|
| 3 days post infection | 4.773 ± 0.446 | 4.650 ± 0.418 | 3.384 ± 0.135 | 3.064 ± 0.447 |
| 5 days post infection | 5.380 ± 0.460 | 5.340 ± 0.434 | 4.155 ± 0.450 | 3.768 ± 0.377 |

2. Effect of the probiotic preparations on the structure of lung tissue in mice infected with H7N9 avian influenza virus: The results of microscopic examination of lung tissue sections showed that on day 3 and day 5 post H7N9 influenza virus infection, compared with the control group taking intragastric administration of PBS, the group taking intragastric administration of *Bifidobacterium animalis* single-bacterium preparation and the group taking intragastric administration of *Bifidobacterium animalis-Bifidobacterium pseudolongum* compound preparation were significantly reduced in pathological injury of influenza virus infection to lung tissue; however, the intragastric administration of the *Bifidobacterium pseudolongum* single-bacterium preparation did not improve pathological injury of influenza virus infection to lung tissue. This further proved the anti-influenza effect of *Bifidobacterium animalis* (FIG. 6A to 6L).

3. Effect of the probiotic preparations on the content of lung cytokines of mice infected with H7N9 avian influenza virus: The determination results of cytokine content in the supernatant of lung tissue sample treatment showed that on day 0 post infection, there was no difference in the content of cytokines TNF-α, IL-1β, IL-6, IL-10, IFN-γ and IFN-β between the control group taking intragastric administration of PBS and the groups taking intragastric administration of three probiotic preparations. On day 3 and day 5 post influenza virus infection, there was significant difference in the content of most of the cytokines measured among the group taking intragastric administration of the *Bifidobacterium animalis* single-bacterium preparation and the group taking intragastric administration of the *Bifidobacterium animalis-Bifidobacterium pseudolongum* compound preparation; but on day 3 and day 5 post infection, the change trend of cytokines was different. First compared with the control group, on day 3 post influenza virus infection, the group taking intragastric administration of the *Bifidobacterium animalis* single-bacterium preparation and the group taking intragastric administration of the *Bifidobacterium animalis-Bifidobacterium pseudolongum* compound preparation showed a significant increasing trend in most of cytokines, but on day 3 and day 5 post infection, the two groups showed a declining trend in cytokine content, and particularly the group taking intragastric administration of the compound preparation showed a more obvious declining trend. Specifically, on day 3 post influenza virus infection, compared with the PBS control group, the group taking intragastric administration of the *Bifidobacterium animalis* single-bacterium preparation showed an obvious increase in the contents of IL-6, IFN-γ, and IFN-β with statistical differences and showed a significant increase in the content of TNF-α; TNF-α, IL-6, IFN-γ, IFN-β increased significantly, and the group taking intragastric administration of the *Bifidobacterium animalis-Bifidobacterium pseudolongum* compound preparation showed a significant increase in the contents of TNF-α, IL-6, IFN-γ, and IFN-β and also showed an obvious increase in the content of IL-10. On day 5 post influenza virus infection, compared with the PBS control group, the group taking intragastric administration of the *Bifidobacterium animalis* single-bacterium preparation showed an obvious decrease in the content of IL-1β and a significant decrease in the content of IL-6, and the group taking intragastric administration of the *Bifidobacterium animalis-Bifidobacterium pseudolongum* compound preparation showed a significant decrease in the contents of TNF-α, IL-10, IL-1β, and IL-6. At different measurement time points, there was no difference in the cytokine content between the group taking the *Bifidobacterium pseudolongum* single-bacterium preparation and the PBS control group (Table 5, FIGS. 7A to 7F).

TABLE 5

Effect of the probiotic preparations on the content of lung cytokines of mice infected with H7N9 avian influenza virus (pg/ml)

| Group | | PBS control | Bifidobacterium pseudolongum | Bifidobacterium animalis group | B. animalis + B. pseudolongum |
|---|---|---|---|---|---|
| Post infection 0 day | TNF-α | 2.870 ± 0.385 | 3.152 ± 0.298 | 3.364 ± 0.676 | 3.046 ± 0.607 |
| | IL-1β | 701.496 ± 128.655 | 691.518 ± 125.705 | 726.348 ± 131.087 | 706.040 ± 152.334 |
| | IL-6 | 32.730 ± 5.088 | 34.654 ± 6.070 | 32.536 ± 5.301 | 32.454 ± 4.842 |
| | IL-10 | 25.124 ± 3.452 | 26.952 ± 3.663 | 26.490 ± 4.176 | 25.892 ± 4.321 |
| | IFN-γ | 64.082 ± 7.927 | 64.646 ± 8.655 | 66.482 ± 10.390 | 65.974 ± 9.104 |
| | IFN-β | 76.766 ± 7.213 | 79.460 ± 7.346 | 77.754 ± 7.138 | 78.197 ± 5.014 |
| 3 days post infection | TNF-α | 8.506 ± 1.796 | 9.246 ± 2.183 | 14.590 ± 2.271 | 14.372 ± 1.546 |
| | IL-1β | 1043.800 ± 98.554 | 918.554 ± 139.072 | 985.438 ± 105.183 | 918.806 ± 138.435 |
| | IL-6 | 138.922 ± 25.185 | 150.710 ± 23.596 | 209.614 ± 21.871 | 229.308 ± 26.887 |
| | IL-10 | 28.824 ± 2.724 | 29.884 ± 4.120 | 29.898 ± 3.566 | 34.516 ± 2.874 |
| | IFN-γ | 75.224 ± 11.451 | 89.538 ± 15.858 | 101.830 ± 12.840 | 121.928 ± 13.258 |
| | IFN-β | 104.995 ± 11.718 | 114.274 ± 16.065 | 141.126 ± 10.635 | 148.042 ± 13.554 |
| 5 days post infection | TNF-α | 21.432 ± 3.714 | 22.844 ± 3.627 | 19.502 ± 2.854 | 16.198 ± 2.173 |
| | IL-1β | 1176.910 ± 147.540 | 1128.034 ± 173.058 | 923.836 ± 160.121 | 784.792 ± 147.886 |
| | IL-6 | 442.314 ± 76.314 | 455.560 ± 64.557 | 312.492 ± 85.979 | 103.950 ± 25.962 |
| | IL-10 | 32.894 ± 2.786 | 35.974 ± 3.910 | 29.846 ± 3.456 | 25.990 ± 2.785 |
| | IFN-γ | 86.652 ± 17.022 | 93.012 ± 17.797 | 89.768 ± 20.736 | 97.362 ± 20.056 |
| | IFN-β | 197.075 ± 22.816 | 203.034 ± 27.750 | 209.430 ± 32.698 | 197.696 ± 26.924 |

4. Effect of the probiotic preparations on the content of serum cytokines in mice infected with H7N9 avian influenza virus: The determination results of the cytokine content in mouse serum showed that on day 0, day 3, and day 5 post H7N9 influenza virus infection, compared with the PBS control group, the group taking intragastric administration of the *Bifidobacterium pseudolongum* preparation showed no difference in the content of each cytokine, and only showed a significant decrease in the content of IL-1β on day 3 post infection and a certain increase in the content of IFN-β on day 5 post infection; however, compared with the control group, the group taking intragastric administration of the *Bifidobacterium animalis* preparation and the group intragastric administration of the *Bifidobacterium animalis-Bifidobacterium pseudolongum* compound preparation showed a significant difference in the contents of most of cytokines on day 3 and day 5 post influenza virus infection. On day 3 post infection, compared with the control group, the group taking intragastric administration of the *Bifidobacterium animalis* preparation showed a significant increase in the contents of TNF-α and IFN-γ and an obvious increase in the content of IFN-β; the group taking intragastric administration of the *Bifidobacterium animalis—Bifidobacterium pseudolongum* compound preparation showed a significant increase in the contents of TNF-α, IL-10, IFN-γ, IL-6, and IFN-β but showed a significant decrease in the content of IL-1β. On day 5 post infection, compared with the PBS control group, the group taking intragastric administration of the *Bifidobacterium animalis* preparation showed a significant decrease in the content of IFN-γ, an obvious increase the contents of TNF-α and IFN-β, and a significant decrease in the content of IL-1β and IL-6, and the group taking intragastric administration of the *Bifidobacterium animalis-Bifidobacterium pseudolongum* compound preparation showed a significant increase in the contents of IFN-γ and IFN-β and a significant decrease in the contents of IL-1β and IL-6 (Table 6, FIGS. 8A to 8F). It can be seen that the *Bifidobacterium animalis-Bifidobacterium pseudolongum* compound preparation group can significantly improve the body's ability to produce interferon, thereby achieving the purpose of eliminating the virus.

TABLE 6

Effect of the probiotic preparations on the content of serum cytokines in mice infected with H7N9 avian influenza virus (pg/ml)

| Group | | PBS control | Bifidobacterium pseudolongum | Bifidobacterium animalis | B. animalis + B. pseudolongum |
|---|---|---|---|---|---|
| Post infection 0 day | TNF-α | 1.403 ± 0.261 | 1.349 ± 0.403 | 1.291 ± 0.306 | 1.434 ± 0.347 |
| | IL-1β | 46.100 ± 0.735 | 45.834 ± 0.472 | 45.889 ± 0.558 | 46.116 ± 0.297 |
| | IL-6 | 6.373 ± 0.822 | 6.037 ± 0.673 | 5.657 ± 0.946 | 5.931 ± 0.617 |
| | IL-10 | 3.644 ± 0.559 | 3.647 ± 0.556 | 3.541 ± 0.538 | 3.509 ± 0.381 |
| | IFN-γ | 1.619 ± 0.622 | 1.651 ± 0.613 | 1.901 ± 0.649 | 1.659 ± 0.591 |
| | IFN-β | 31.734 ± 3.116 | 30.539 ± 2.317 | 31.040 ± 2.853 | 31.723 ± 3.401 |
| 3 days post infection | TNF-α | 1.234 ± 0.324 | 1.314 ± 0.413 | 3.366 ± 0.973 | 4.807 ± 0.990 |
| | IL-1β | 53.246 ± 2.708 | 47.781 ± 2.650 | 50.884 ± 2.052 | 45.870 ± 2.393 |
| | IL-6 | 21.691 ± 5.281 | 20.364 ± 5.344 | 25.011 ± 5.501 | 69.451 ± 12.797 |
| | IL-10 | 3.377 ± 0.193 | 3.384 ± 0.377 | 3.899 ± 0.882 | 5.243 ± 0.733 |
| | IFN-γ | 1.750 ± 0.577 | 1.404 ± 0.300 | 21.186 ± 13.079 | 58.720 ± 29.046 |
| | IFN-β | 31.292 ± 3.087 | 30.032 ± 2.748 | 37.675 ± 3.562 | 40.666 ± 3.412 |
| 5 days post infection | TNF-α | 1.321 ± 0.212 | 1.413 ± 0.282 | 2.006 ± 0.483 | 1.571 ± 0.426 |
| | IL-1β | 65.026 ± 3.797 | 65.359 ± 3.093 | 60.184 ± 3.798 | 58.967 ± 2.768 |
| | IL-6 | 54.333 ± 14.122 | 45.080 ± 16.129 | 35.990 ± 11.465 | 10.583 ± 4.714 |
| | IL-10 | 3.583 ± 0.714 | 3.369 ± 0.549 | 3.896 ± 0.836 | 3.240 ± 0.716 |
| | IFN-γ | 3.306 ± 0.553 | 3.099 ± 0.844 | 8.273 ± 1.693 | 7.144 ± 1.122 |
| | IFN-β | 35.080 ± 6.752 | 41.950 ± 7.062 | 42.102 ± 5.712 | 52.002 ± 6.496 |

What is claimed is:

1. A method for treating avian influenza virus H7N9 infection, comprising
    preparing a composition comprising *Bifidobacterium animalis* ATCC Accession No. 25527, wherein an effective bacterial concentration of the composition is equal to or greater than $1\times10^9$ CFU/ml, and administering the composition to a subject in need of treatment for avian influenza virus H7N9 infection, and regulating cytokine-related immune response and inhibiting proliferation of avian influenza virus H7N9 in the subject.

2. A method of claim 1, wherein the immune response in the subject is regulated by stimulating interferon production.

3. The method of claim 1, wherein the composition further comprises *Bifidobacterium pseudolongum* ATCC Accession No. 25526, and the effective total bacterial concentration of *Bifidobacterium animalis* ATCC Accession No. 25527 and *Bifidobacterium pseudolongum* ATCC Accession No. 25526 is equal to or greater than $1\times10^9$ CFU/ml.

4. The method of claim 3, wherein a ratio of the effective bacterial concentration of the *Bifidobacterium animalis* ATCC Accession No. 25527 to the *Bifidobacterium pseudolongum* ATCC Accession No. 25526 in the composition is 1:0.5 to 1:2.

* * * * *